United States Patent [19]

Boudjouk

[11] Patent Number: 4,827,009

[45] Date of Patent: May 2, 1989

[54] HYDROSILATION PROCESS

[75] Inventor: Philip R. Boudjouk, Fargo, N. Dak.

[73] Assignee: North Dakota State University, Fargo, N. Dak.

[21] Appl. No.: 92,678

[22] Filed: Sep. 3, 1987

[51] Int. Cl.$^4$ ................................................ C07F 7/08
[52] U.S. Cl. ................................. 556/979; 204/157.62
[58] Field of Search ..................... 556/479; 204/157.62

[56] References Cited

U.S. PATENT DOCUMENTS

| | | | |
|---|---|---|---|
| 3,907,850 | 9/1975 | Capka et al. | ..................... 556/479 X |
| 4,447,633 | 5/1984 | Boudjouk | ............................. 556/479 |

FOREIGN PATENT DOCUMENTS 1438949  6/1976  United Kingdom ................ 556/479

OTHER PUBLICATIONS

"Doklady Akad. Nauk SSSR", 127, No. 2, pp. 352–355, 1959.
Mel'nitskii, I. A.; Kirilyuk, B. A.; Kiladze, T. K.; Kantor, E. A.; Rakhmankulov, D. L.; Zh. Obshch. Khim., 1984, vol. 54. 372–375 (Chem. Abstr., 1984, 101, 23,572), translated Plenum Publishing Corp., copyright 1984, pp. 331, 334.
Cornish, A. J.; Lappert, M. F.; Nile, T. A., J. Organomet. Chem., 1977, vol. 132, 133–148; Salimgareeva, L.; Kaverin, V. V.; Juriev, V. P., ibid., 1978, vol. 148, 23–27; Lappert, M. F.; Nile, T. A.; Takahashi, S.; J. Organomet. Chem., 1974, vol. 72, 425–439.
Moldavaskaya, N. A.; Khavatova, T. P.; Skvortsov, N. K.; Reikjsfel'd, V. O.; Zh. Obshch. Khim., 1980, vol. 50, 851–854.
Yamamoto, K.; Hayashi, T.; Uramoto, Y.; Ito, R.; Kumada, M., J. Organomet. Chem., 1976, vol. 118, 331–348.
Kiso, Y.; Kumada, M.; Tamao, K.; Umeo, M., ibid., 1973, vol. 50, 297–310.
Faltynek, R. A.; Chem. Abstr., 1985, vol. 103, 161668j.
Reikhsfel'd, V. D., Chem. Abstr., 1985, vol. 102, 46274v.
Gailyunas, G.; Yusupova, F. G.; Isaeva, L. S.; Peganova, T. A.; Kayumov, F. F.; Yur'ev, V. P., Zh. Obshch. Khim., 1984, vol. 54(10), 2269–2272, (Chem. Abstr., 1985, vol. 102, 149,477).
Capka, M.; Macho, V., Chem. Abstr., 1979, vol. 90, 104114.
Hetfleis, J.; Vaisarova, V., Chem. Abstr., 1978, vol. 89: 43761d.
Capka, M.; Svoboda, P.; Hetfleis, J.; Bazant, V.; Bazant, P.; Bazantova, V.; Bazant, J. Chem. Abstr., 1976, vol. 84: 44344d.
Cukovskaja, E. C.; Freijdlina, R. C., Izv. Akad, Nauk. Otd. Chim. Nauk., 1963, 731. Chem Abstr., 1963, vol. 59: 7551g.
Lappert and Nile, "Homogenous Catalysts", Journal of Organomet. Chem. 102 (1975), 543–550.
Rieke, R. D., Acc. Chem. Res. 1977, vol. 10, p. 301.

*Primary Examiner*—Paul F. Shaver
*Attorney, Agent, or Firm*—Price, Heneveld, Cooper, DeWitt & Litton

[57] ABSTRACT

The specification discloses catalyzing hydrosilation reactions with nickel dispersed in an inert reaction medium, where the nickel is prepared by reacting a nickel halide with an alkali metal. The hydrosilation reaction and the preparation of the nickel dispersion are presently conducted in the presence of ultrasound.

21 Claims, No Drawings

HYDROSILATION PROCESS

This invention was made with government support under AFOSR-84-0008 awarded by the Air Force. The Government of the United States has certain rights in this invention.

BACKGROUND OF THE INVENTION

The present invention relates to hydrosilation reactions (often spelled "hydrosilylation" in the literature). It is well established that the addition of Si—H bonds to C=C or C≡C bonds is catalyzed by various transition metals, their complexes and salts. In most cases, Speier's chloroplatinic acid and Wilkinson's rhodium complexes are the most effective catalysts, compared to the carbonyls of iron, cobalt, chromium, manganese and rhodium, and the complexes of platinum, palladium, iridium, rhodium and copper. Using Speier's chloroplatinic acid as a catalyst, hydrosilation reactions proceed with a great degree of efficiency, giving high yields, at room temperature.

Because platinum and rhodium are very expensive, it would be desirable to catalyze hydrosilation reactions with the less expensive transition metal, nickel. However, even hydrosilation pioneers such as Speier have been unable to get nickel to work as a practical matter at approximately room temperature.

Raney nickel is an excellent hydrogenation catalyst. However, artisans have not heretofore been able to use nickel as a practical commercial hydrosilation catalyst.

Petrov et al., Izvest. Akad. Nauk S.S.S.R., Ser. Khim. 1956, 256; Chem. Abstr., 1956, 50, 13726d, reported as early as 1956 that Raney nickel catalyzed the addition of trichlorosilane to acrylonitrile at 160 degrees C. for four hours in a sealed tube, yielding 13% $\beta$-cyanoethyltrichlorosilane. However at 150 degrees C., most hydrosilation reactions will proceed to 15% yield even without a catalyst.

In 1970, Kumada et al., Chem. Comm., 1970, 611, reported that some nickel chloride phosphine complexes catalyzed the addition of methyldichlorosilane to a variety of olefins at 120 degrees C. for 20 hours to give the hydrosilation product in 55 to 87% yield. As above, a reaction at such high temperatures for such a long period of time is commercially impractical and certainly fails to suggest the use of nickel as a substitute for Speier's chloroplatinic acid or Wilkinson's rhodium complexes which facilitate hydrosilation rapidly and at room temperature.

The inoperability of nickel as a room temperature catalyst for hydrosilation reactions has been a great frustration to hydrosilation chemists, with very significant economic consequences. Billions of dollars in hydrosilation products have been produced using the more expensive, but operable platinum and rhodium catalysts.

SUMMARY OF THE INVENTION

I have surprisingly found that a dispersion of zero valent nickel effectively catalyzes hydrosilation reactions at room temperature. In a preferred embodiment, a zero valent nickel dispersion is prepared by reacting a nickel halide with an alkali metal. Most preferably, the hydrosilation reactions are conducted under exposure to ultrasonic energy.

These and other objects, advantages and features of the invention will be more fully understood and appreciated by reference to the Description of the Preferred Embodiment.

DESCRIPTION OF THE PREFERRED EMBODIMENT

The Nickel Catalyst

In the preferred embodiment, the nickel catalyst used to catalyze hydrosilation reactions is preferably prepared by reacting a nickel halide with an alkali metal in an inert liquid reaction medium. It is presently believed that the key to the operability of this preferred nickel catalyst is its zero valent state at its reactive surfaces.

Successful hydrogenation nickel catalysts, which have been found inoperable in hydrosilation, do not exhibit a zero valent state at their reactive surfaces. For example, Raney nickel is prepared by dissolving nickel in aluminum, and then dissolving the aluminum with sodium hydroxide. The exposed surface of the nickel is saturated with hydrogen creating at least a surface layer of nickel hydride. The surface nickel in Raney nickel is believed not to be substantially zero valent nickel.

Catalytic nickel has also been prepared by placing nickel oxide on carbon and then reducing the nickel with hydrogen. Again, a nickel hydride surface is created such that at least the surface nickel is not zero valent nickel.

Mossy nickel has proven inoperable in the catalysis of hydrosilation reactions, perhaps because its surface has been oxidized, or perhaps because it does not constitute a dispersion.

The zero valent nickel used in the process of the present invention is dispersed in an inert reaction medium. The particle size of the dispersed nickel is typically less than 20 microns.

Once prepared, the zero valent nickel used in the present invention should be kept under an inert gas. It can be reused, though it should be washed with an inert solvent such as tetrahydrofuran after every three or four uses.

Preferably, the reactants used in the preparation of the nickel catalyst are exposed to ultrasonic vibrations at a frequency sufficient to produce cavitation. This creates the desired agitation effect. A frequency of from about 16 KHz to about 1000 KHz encompasses the ultrasonic range. I worked specifically at 50 to 60 KHz with a Branson Model B-220 ultrasonic cleaner (117 volts, 125 watts), but that equipment and ultrasonic range are not critical.

The preferred nickel hydride is nickel iodide and the preferred alkali metal is lithium. A typical nickel catalyst preparation is illustrated in Example 1 below:

EXAMPLE 1

Nickel catalyst preparation 4.4 grams or 14 mmol of nickel iodide and 0.2 grams or 28 mmol of lithium powder were added to an oven dried 100 milliliter single neck round bottom flask equipped with an argon inlet and condenser. After adding 10 ml of tetrahydrofuran (THF) distilled under nitrogen from sodium-benzophenone, the flask was placed in an ultrasonic bath at a point that caused the most agitation in the flask. The mixture was sonicated for 15 minutes. The sonication was stopped and the flask was cooled to 0 degrees C.

The resulting dispersion of nickel was used in subsequent hydrosilation reactions. The dispersed nickel showed no noticeable loss in reactivity upon recycling, provided the powder was washed with THF after three or four runs.

The Hydrosilation Reaction

Zero valent nickel in accordance with the foregoing is an effective hydrosilation catalyst for a variety of hydrosilanes and alkenes or alkynes. The use of ultrasonic vibration during the reaction improves the efficiency and yield of hydrosilation product obtained.

As is well-known, the most reactive of these are the terminal alkenes or terminal alkynes of the general formulas:

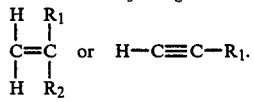

Typically, hydrosilation reactions involve terminal alkenes (terminal olefins). Reactivity drops if the unsaturated bond is not located in the terminal position, or if the terminal carbon is capped with a substituent other than hydrogen, e.g., a halogen or hydroxy group.

This general truth also seems applicable in the present invention. For example, crotonitrile ($CH_3CH=CHCN$) and cinnamonitrile ($PhCH=CHCN$) could not be reacted with hydrosilanes in the presence of the nickel catalyst, even when ultrasonic vibrations were applied. Capping the terminal carbon of the unsaturated bond with a large substituent such as the phenyl and methyl groups of these compounds creates a steric hindrance to reaction. Thus, uncapped (except with hydrogen atoms) terminal olefins are generally preferred in hydrosilation reactions.

The catalyst is effective both with activated and nonactivated terminal olefins. Basically, an activated olefin is one that includes an electrophilic substituent on one side of the olefinic bond, without capping the terminal carbon. Examples of such activated olefins include:

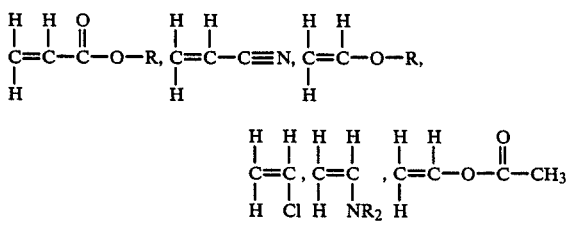

Nonactivated olefins lack such electrophilic substituents. Examples of nonactivated olefins include 1-alkenes and styrene. When nonactivated terminal olefins are to be reacted with hydrosilanes, an activator should be incorporated in the reaction mixture. An example of such an activator is triphenyl phosphine.

Trichlorosilane proved to be the most reactive hydrosilating agent. Methyldichlorosilane was less reactive, and less reactive towards vinyl acetate. Replacement of two chlorine atoms by two methyl substituents decreased yields substantially for both sonicated and nonsonicated, i.e., mechanically stirred reaction mixtures.

A number of experiments were conducted using various hydrosilanes and terminal olefins. The results of these experiments are reported in Examples 2–26 below and are summarized in Table 1:

TABLE 1

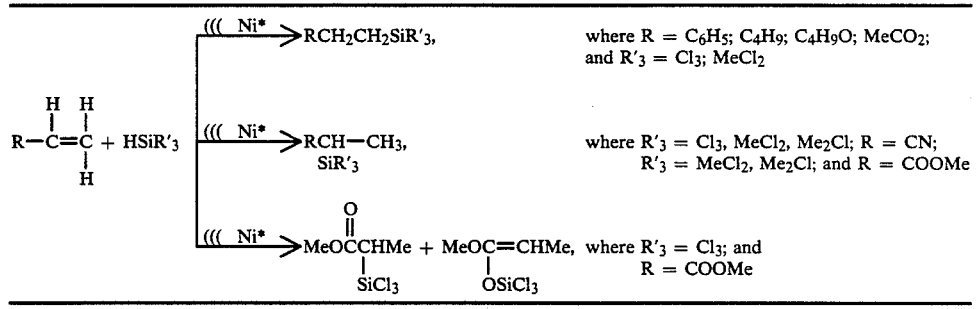

Ni* = activated nickel in THF at 0–25 degrees C.
((( = ultrasonic vibration, though not used in every example.
Me = $CH_3$ throughout this specification.

EXAMPLES

Hydrosilation Reactions

EXAMPLE 2

A dispersed nickel catalyst was prepared in accordance with Example 1 above. After the flask was cooled to 0 degrees C., a mixture of acrylonitrile (40 mmol) and methyldichlorosilane (50 mmol) was added dropwise to the dispersion. After addition was complete, the flask was connected to a mercury barometer to contain volatile reactants. The mixture was warmed to room temperature while sonicating. The bath temperature for sonication was maintained at 0–25 degrees C. by a four inch muffle fan mounted on the side of the cleaner and ice in the ultrasonic bath. The reaction mixture was filtered and the filtrate evaporated at low pressure to remove THF and excess silane. 6.5 g α-Cyanoethylmethyldichlorosilane[1] (96% yield) was isolated by distillation (38 degrees C./0.6 torr).

[1] $CH_3CHCN$
       |
       $SiCl_2CH_3$

The results for Example 2 and Examples 3–26 are summarized in Table 2 below. Each reaction was conducted using the nickel catalyst of Example 1. With the exception of the variables noted in the Table, the reactions were conducted in accordance with the procedure outlined in Example 2 above. In the column labeled "condition," the use of ultrasound is indicated by "US" while the use of mechanical stirring is indicated by "Stir." The time in hours over which the reaction was conducted is indicated, along with the yield of end product. In many cases, two products were obtained, as is indicated. In Examples 3–7, catalytic quantities of triphenylphosphine were used as an activator, since the olefins in those Examples are all nonactivated olefins. Without using an activator, the yields would be about 5% rather than the more substantial yields reported.

TABLE 2

| Exam | Olefins | Silane | Condition | time (h) | Product | Yield, % |
|---|---|---|---|---|---|---|
| 2 | acrylonitrile | HSiMeCl$_2$ | US | 2 | CH$_3$CHSiMeCl$_2$<br>\|<br>CN | 96 |
| 3 | 1-hexene | HSiCl$_2$ | US | 2 | n-C$_6$H$_{13}$SiCl$_3$ | 62 |
| 4 | 1-hexene | HSiCl$_3$ | US | 3 | n-C$_6$H$_{13}$SiCl$_3$ | 81 |
| 5 | 1-hexene | HSiCl$_3$ | stir | 20 | n-C$_6$H$_{13}$SiCl$_3$ | 75 |
| 6 | styrene | HSiCl$_3$ | US | 2 | PhCH$_2$CH$_2$SiCl$_3$ | 88 |
| 7 | styrene | HSiCl$_3$ | stir | 20 | PhCH$_2$CH$_2$SiCl$_3$ | 58 |
| 8 | acrylonitrile | HSiCl$_3$ | US | 1 | CH$_3$CHSiCl$_3$<br>\|<br>CN | 70 |
| 9 | acrylonitrile | HSiCl$_3$ | stir | 2 | CH$_3$CHSiCl$_3$<br>\|<br>CN | 75 |
| 10 | acrylonitrile | HSiMeCl$_2$ | stir | 2 | CH$_3$CHSiMeCl$_2$<br>\|<br>CN | 74 |
| 11 | acrylonitrile | HSiMe$_2$Cl | US | 2 | CH$_3$CHSiMe$_2$Cl | 15 |
| 12 | acrylonitrile | HSiMe$_2$Cl | stir | 20 | CH$_3$CHSiMe$_2$Cl<br>\|<br>CN | 3 |
| 13 | methylacrylate | HSiCl$_3$ | US | 2 | CH$_3$CHSiCl$_3$<br>\|<br>COOMe<br><br>CH$_3$CH=COSiCl$_3$<br>\|<br>OMe | 74[c] |
| 14 | methylacrylate | HSiCl$_3$ | stir | 2.5 | CH$_3$CHSiCl$_3$<br>\|<br>COOMe<br><br>CH$_3$CH=COSiCl$_3$<br>\|<br>OMe | 65[c] |
| 15 | methylacrylate | HSiMeCl$_2$ | US | 3 | CH$_3$CHSiMeCl$_2$<br>\|<br>COOMe | 87 |
| 16 | methylacrylate | HSiMeCl$_2$ | stir | 20 | CH$_3$CHSiMeCl$_2$<br>\|<br>COOMe | 63 |
| 17 | methylacrylate | HSiMe$_2$Cl | US | 8 | CH$_3$CHSiMe$_2$Cl<br>\|<br>COOMe | 16 |
| 18 | methylacrylate | HSiMe$_2$Cl | stir | 20 | CH$_3$CHMe$_2$Cl<br>\|<br>COOMe | 3 |
| 19 | vinylacetate | HSiCl$_3$ | US | 3 | CH$_3$COOCH$_2$CH$_2$SiCl$_3$ | 42 |
| 20 | vinylacetate | HSiCl$_3$ | stir | 12 | CH$_3$COOCH$_2$CH$_2$SiCl$_3$ | 10 |
| 21 | vinylacetate | HSiMeCl$_2$ | US | 12 | CH$_3$COOCH$_2$CH$_2$SiMeCl$_2$ | 5 |
| 22 | vinylacetate | HSiMeCl$_2$ | stir | 8 | CH$_3$COOCH$_2$CH$_2$SiMeCl$_2$ | 0 |
| 23 | vinylbutyl ether | HSiCl$_3$ | US | 4 | n-C$_4$H$_9$OCH$_2$CH$_2$SiCl$_3$ | 78 |
| 24 | vinylbutyl ether | HSiCl$_3$ | stir | 20 | n-C$_4$H$_9$OCH$_2$CH$_2$SiCl$_3$ | 53 |
| 25 | vinylbutyl ether | HSiMeCl$_2$ | US | 4 | n-C$_4$H$_9$OCH$_2$CH$_2$SiMeCl$_2$ | 71 |
| 26 | vinylbutyl | HSiMeCl$_2$ | stir | 20 | n-C$_4$H$_9$OCH$_2$CH$_2$SiMeCl$_2$ | 48 |

TABLE 2-continued

| Exam | Olefins | Silane | Condition, time (h) Product | Yield, % |
|------|---------|--------|------------------------------|----------|
|      | ether   |        |                              |          |

[a] All reactions were at 0–25 degrees C. using a 0.04:0.05:8.5 × $10^{-3}$ moles of olefin/silane/activated nickel in 10 ml of THF. In Examples 3-7, .5 grms (2 × $10^{-3}$ moles) triphenyl phosphine were added.
[b] Yields are based on material isolated by distillation.
[c] Total yields of O—silated and C—silated adducts.

The substantial effectiveness of nickel catalyst in accordance with the present invention is illustrated by the above Examples. In all cases, improved yields were obtained using ultrasonic vibration rather than mechanical stirring. Hydrosilations of methylacrylate with trichlorosilane proceeded in good yield but led to O-silated (from 1,4 addition) and C-silated (from 1,2 addition) products (runs 12 and 13) in approximately equal quantities with the O-silated isomer usually dominating. Methyldichlorosilane is more selective however, forming only the 1,2 adduct (runs 14 and 15).

Surprisingly, hydrosilation reactions proceed at room temperature or below using the method of the present invention. The experimental work was conducted at temperatures between 0 and 25 degrees C. This is a very important advantage of the present method, but should not be interpreted in the broader aspects of the invention to rule out the possibility of someone using the present invention to facilitate hydrosilation reactions at higher temperatures.

The surprising reactivity of activated dispersed nickel in accordance with the present invention in hydrosilation reactions, and the further enhancement of that activity through the use of ultrasonic vibrations, has tremendous commercial implications. This is believed to be a pioneer breakthrough in hydrosilation catalysis. Accordingly, it is to be remembered that the above is merely illustrative of the preferred embodiments of the invention and that various changes and alterations can be made without departing from the spirit and broader aspects of the invention.

The embodiments of the invention in which an exclusive property or privilege is claimed are defined as follows:

1. A method for catalyzing hydrosilation reactions by exposing the reactants to a dispersion of zero valent elemental nickel in an inert reaction medium.

2. The method of claim 1 including the preparation of said dispersion of zero valent nickel by reacting nickel halide with a reactive alkali metal in an inert reaction medium.

3. The method of claim 2 in which said nickel halide and alkali metal are exposed to ultrasonic energy during reaction.

4. The method of claim 3 in which said hydrosilation reactants and said zero valent nickel are exposed to ultrasonic energy during reaction.

5. The reaction of claim 4 in which one of said hydrosilation reactants is nonactivated olefin and in which an activator is introduced into said reaction medium.

6. The reaction of claim 5 in which said activator is triphenyl phosphine.

7. The method of claim 1 in which said hydrosilation reactants and said zero valent nickel are exposed to ultrasonic energy during reaction.

8. The reaction of claim 1 in which one of said hydrosilation reactants is nonactivated olefin and in which an activator is introduced into said reaction medium.

9. A method for catalyzing hydrosilation reactions by exposing the reactants to a dispersion of nickel in an inert medium, wherein said nickel has been prepared by the reaction of nickel halide with an alkali metal in an inert reaction medium.

10. The method of claim 9 in which said nickel halide and alkali metal are exposed to ultrasonic energy during reaction.

11. The method of claim 10 in which said hydrosilation reactants and said nickel are exposed to ultrasonic energy during reaction.

12. The reaction of claim 11 in which one of said hydrosilation reactants is nonactivated olefin and in which an activator is introduced into said reaction medium.

13. The method of claim 9 in which said hydrosilation reactants and said nickel are exposed to ultrasonic energy during reaction.

14. The reaction of claim 9 in which one of said hydrosilation reactants is nonactivated olefin and in which an activator is introduced into said reaction medium.

15. The method of claim 11 in which the particle size of the nickel particles in said dispersion of nickel is typically less than 20 microns.

16. The method of claim 10 in which the particle size of the nickel particles in said dispersion of nickel is typically less than 20 microns.

17. The method of claim 9 in which the particle size of the nickel particles in said dispersion of nickel is typically less than 20 microns.

18. The method of claim 4 in which the particle size of the nickel particles in said dispersion of nickel is typically less than 20 microns.

19. The method of claim 3 in which the particle size of the nickel particles in said dispersion of nickel is typically less than 20 microns.

20. The method of claim 2 in which the particle size of the nickel particles in said dispersion of nickel is typically less than 20 microns.

21. The method of claim 1 in which the particle size of the nickel particles in said dispersion of nickel is typically less than 20 microns.

* * * * *